US009395265B2

(12) United States Patent  
O'Shaughnessy et al.

(10) Patent No.: US 9,395,265 B2
(45) Date of Patent: Jul. 19, 2016

(54) FULL HEAD SURROGATE WITH LIVE NEURONS FOR HELMET TESTING AND EVALUATION

(71) Applicants: Thomas O'Shaughnessy, Arlington, VA (US); Ryan McCulloch, Alexandria, VA (US); Amit Bagchi, Rockville, MD (US); Kirth Simmonds, Clinton, MD (US)

(72) Inventors: Thomas O'Shaughnessy, Arlington, VA (US); Ryan McCulloch, Alexandria, VA (US); Amit Bagchi, Rockville, MD (US); Kirth Simmonds, Clinton, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 60 days.

(21) Appl. No.: 14/576,689

(22) Filed: Dec. 19, 2014

(65) Prior Publication Data

US 2016/0178476 A1  Jun. 23, 2016

(51) Int. Cl.
*C12M 1/34* (2006.01)
*C12M 3/00* (2006.01)
*G01M 7/08* (2006.01)
*C12M 1/12* (2006.01)
*G01N 33/50* (2006.01)

(52) U.S. Cl.
CPC .............. *G01M 7/08* (2013.01); *C12M 25/04* (2013.01); *G01N 33/5058* (2013.01)

(58) Field of Classification Search
CPC .... G01M 7/08; G01N 33/5058; C12M 25/04; C12M 25/14; C12M 37/02; C12M 23/22; C12M 23/26

USPC ........................................................ 435/287.1
See application file for complete search history.

(56) References Cited

U.S. PATENT DOCUMENTS

| | | | | |
|---|---|---|---|---|
| 4,748,124 A | * | 5/1988 | Vogler | C12M 23/24 435/297.1 |
| 4,976,695 A | * | 12/1990 | Wang | A61M 39/0208 600/573 |
| 2005/0100873 A1 | * | 5/2005 | Meythaler | G09B 23/30 702/150 |
| 2012/0330599 A1 | * | 12/2012 | Roberts | G01R 33/0064 702/150 |
| 2014/0273062 A1 | | 9/2014 | O'Shaughnessy et al. | |

OTHER PUBLICATIONS

Arun P, Spadaro J, John J, Gharavi RB, Bentley TB, Nambiar MP. (2011) "Studies on blast traumatic brain injury using in-vitro model with shock tube." Neuroreport 22: 379-384.

Effgen GW, Hue CD, Vogel III E, Panzer MB, Meaney DF, Bass CR, Morrison III B. (2012) "A multiscale approach to blast neurotrauma modeling: part II: methodology for inducing blast injury to in vitro models." Frontiers in Neurology 3: 1-10.

* cited by examiner

*Primary Examiner* — Michael Hobbs
(74) *Attorney, Agent, or Firm* — US Naval Research Laboratory; Roy Roberts (57) ABSTRACT

A system for testing a helmet includes a simulated skull comprising a cranial cavity; a brain surrogate disposed inside the cranial cavity; and a cell pack comprising at least one culture well suitable for three-dimensional growth of live neurons therein, the cell pack comprising a retaining plate having at least one opening exposing a portion of a flexible membrane containing the at least one cell culture well, the exposed membrane portion being substantially flush with an exterior surface of the retaining plate, wherein the brain surrogate is configured to closely surround the cell pack inside the simulated skull. Also disclosed is a method of using the system.

15 Claims, 6 Drawing Sheets

FULL HEAD SURROGATE WITH LIVE NEURONS FOR HELMET TESTING AND EVALUATION

RELATED APPLICATIONS

This patent application is related to commonly-owned U.S. patent application Ser. No. 14/486,622 filed on Sep. 15, 2014 as well as commonly-owned US Patent Application Publication No. 2014/0273062 filed on Mar. 5, 2014, each of which is incorporated herein by reference.

BACKGROUND

Current helmet testing is designed to assess resistance to ballistic impacts from small arms and fragments, and is conducted on metallic head forms covered with a layer of clay. Performance criteria for the helmet is on a pass/fail basis determined on lack of penetration of the helmet and a deformation of the clay layer that does not exceed a specified depth. Blunt trauma testing is done using a drop tower, again with simple criteria and metallic head forms. No standardized method exists for evaluating helmets for mitigating blast-induced mild traumatic brain injury. A need exists for improved techniques for evaluating helmet materials for protection against insults that would result in a traumatic brain injury (TBI) or mild traumatic brain injury (mTBI).

BRIEF SUMMARY

In one embodiment, a system for testing a helmet includes a simulated skull comprising a cranial cavity; a brain surrogate disposed inside the cranial cavity; and a cell pack comprising at least one culture well suitable for three-dimensional growth of live neurons therein, the cell pack comprising a rigid retaining plate having at least one opening exposing a portion of a flexible membrane containing the at least one cell culture well, the exposed membrane portion being substantially flush with an exterior surface of the retaining plate, wherein the brain surrogate is configured to closely surround the cell pack inside the simulated skull.

Another embodiment includes subjecting a system of the above embodiment to a physical insult and measuring a result of the physical insult

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

The terms "protective headgear" and "helmet" are used interchangeably to refer to items designed to be worn on the human head for physical protection against impact, blast, and/or ballistic damage, and the like.

The term three-dimensional (or 3D) culture refers to the growth of cells in culture with a thickness greater than a monolayer of cells, e.g., in a culture a few cells to centimeters in thickness. Preferably, in the case of a culture including neurons, the neurons are in communication with one another.

Overview

Described herein is a system comprising a surrogate head and brain that incorporates a sealed 'cell pack' containing independent cultures of neurons in a three-dimensional matrix (for example, a collagen matrix) for use in testing helmets and other head gear for protection of cells from damage during a blast event, impact, or ballistic hit. The anthropomorphic nature of the system allows for testing of virtually any type of head gear and exposure to most types of insults that would result in a traumatic brain injury (TBI). After exposure to the insult, the neuronal cells' function and viability are assessed and compared to controls in order to determine if the head gear was able to mitigate damage to the cells. In addition to its use in testing protective headgear, the system described here also provides a platform for the study of mild traumatic brain injury (mTBI).

At the US Naval Research Laboratory (NRL), instrumented surrogate model headforms made of compliant skull and polymeric materials, which emulate brain biomechanical properties, have been able to provide pressure and acceleration data for blast and ballistic loading with and without a helmet. However, such systems provide purely mechanical data which are not directly linked with neural cell injuries, except through correlations with data from live animals subjected to similar blast and ballistic loadings.

While the present standard for helmet testing does not take into account blast wave effects, there are systems that are being used to gather this type of data. A primary example of this is the NRL's own GelMan-Head surrogate that places accelerometers and pressure sensors within and around a gel-based brain, skull, tissue model of the human head in order to measure the forces resulting in key locations in response to real and simulated blast waves. Helmet systems placed on the GelMan surrogate are tested to determine their ability to reduce these measured forces. However, this model system still lacks the ability to examine cellular level effects.

Current blunt impact helmet testing utilizes a metal head form that approximates the weight and size of a human head with an accelerometer mounted at the centroid of the headform. A helmet with padding and suspension in place are affixed to a head form on a drop tower. Subsequently, drops to a solid anvil are conducted from pre-determined heights. Performance criteria for the helmet is pass/fail based on acceleration of the head form centroid not exceeding a threshold value. The impacts are conducted to achieve standard velocities of 10.0, 14.1, or 17.3 feet per second (fps) at impact.

The commonly-owned U.S. patent application Ser. No. 14/486,622 filed on Sep. 15, 2014 describes a modular system for testing helmet and optionally helmet padding and/or suspension materials for their ability to protect live neurons from the effects of simulated blast waves or blunt impacts. That apparatus includes parts to secure neuronal cultures, in a variety of formats, behind layers of helmet material, suspension padding, and simulated skin, skull, and brain layers. However, it lacks the geometries required for directly testing head gear as now described herein. Now disclosed is a full head/brain surrogate that utilizes a cell pack adapted for testing the ability of helmets and other headgear to prevent direct cell damage in a blast, impact, or ballistic event.

Cell Culture Pack

Aspects relating to suitable cell culture packs are described in commonly-owned U.S. patent application Ser. No. 14/486, 622 filed on Sep. 15, 2014 as well as commonly-owned US Patent Application Publication No. 2014/0273062, each of which is incorporated by reference. The cell cultures can be sealed at the time of culture to maintain sterility, thus allowing the cells to be removed from a cell culture laboratory for testing in a multitude of scenarios and environmental conditions, but the packs preferably feature gas-permeable membranes to allow for exchange of oxygen and carbon dioxide to maintain viability of the cells. Such packs preferably allow for a three-dimensional (3D) cell culture that better mimics the in vivo cellular environment under in vitro conditions as compared to traditional growth in a monolayer. Furthermore, such a cell pack allows for the passage of mechanical forces (pressure, force, acceleration, strain, etc.) into the culture chamber via a flexible membrane.

A first exemplary cell culture pack is now described. The cell culture pack includes a main body constructed of plastic (for example, polysulfone or acrylic) with dimensions of 2 in×2 in×0.5 in. It includes four culture chambers, each comprising a well with a diameter of 0.5 in. Top and bottom metal plates, typically aluminum, are tapped for five screws (6-32 thread). A bottom membrane layer of 1/32 in clear silicone rubber is positioned against the plastic. Another aluminum layer (1/8 in thick) is positioned against the rubber and five screws are put in place to hold this bottom layer on the chamber. The aluminum base layer, or retaining plate, has five holes matching the culture chambers. This allows for passage of a pressure wave directly through the silicone membrane layer and into the culture chamber. Furthermore, the exposed silicone beneath the cell culture allows for passage/exchange of both $CO_2$ and $O_2$ to maintain the viability of the cells in culture. However the silicone rubber membrane stops the passage of bacteria and thus maintains the sterility of the culture. The chambers are filled with a collagen hydrogel with suspended primary culture neural cells. The collagen is allowed to "gel" on the bottom surface of the chamber (the silicone layer) and the rest of the chamber is filled with culture media. A silicone membrane (identical to the bottom one) is placed on the top of the chamber, and then a final top aluminum plate is placed. The top layers are then affixed with five screws. The entire chamber may then be placed in an incubator to maintain temperature and proper $CO_2$ saturation. The chamber may be removed at any point for testing as sterility is maintained in the chamber wells via the top and bottom silicone layers. The system may be sterilized by placing all of the components in an autoclave. Alternately, UV exposure or a 70% ethanol mixture can be used.

Figure 1A:
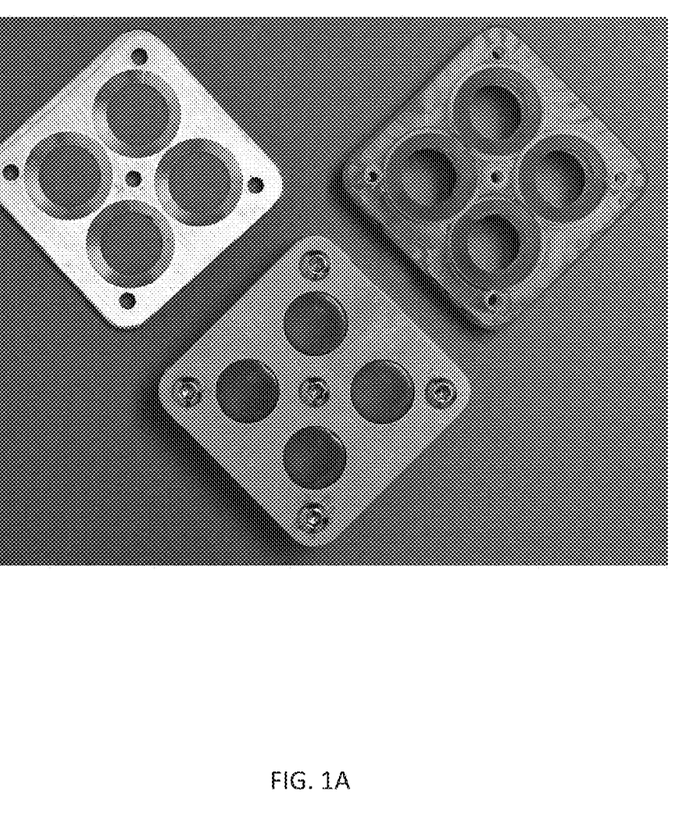
FIG. 1A, clockwise from bottom-most component, shows the bottom plate of an exemplary cell pack along with the silicone rubber membrane layer that forms the bottom of each cell culture well, flush with the aluminum retaining plate. The top left component is a retaining plate showing the chamfer around the openings for the wells. The top right component is the plastic main body of the disassembled exemplary cell pack.

It was found that thickness of the metal plates in above-described configuration resulted in a gap between the plate and the membrane surface, which hindered acoustic coupling. Thus, in an embodiment suited for use in an anthropomorphic head system, the cell culture pack was modified as follows. On the bottom side of the main body, an inverse chamfer was cut 1/8" deep around each of the four wells, thus reducing the body to 3/8" thick while maintaining the well at 1/2" thick. The aluminum plate holding the silicone gasket in place had a matching chamfer around each well. When assembled, this had the effect of stretching the membrane tight across each well and making it flush with the outer surface of the aluminum plate seen in FIGS. 1A and 1B. These adaptations served to improve acoustic coupling of forces from the forward portion of the gel-based brain into the cell cultures.

Figure 1B:
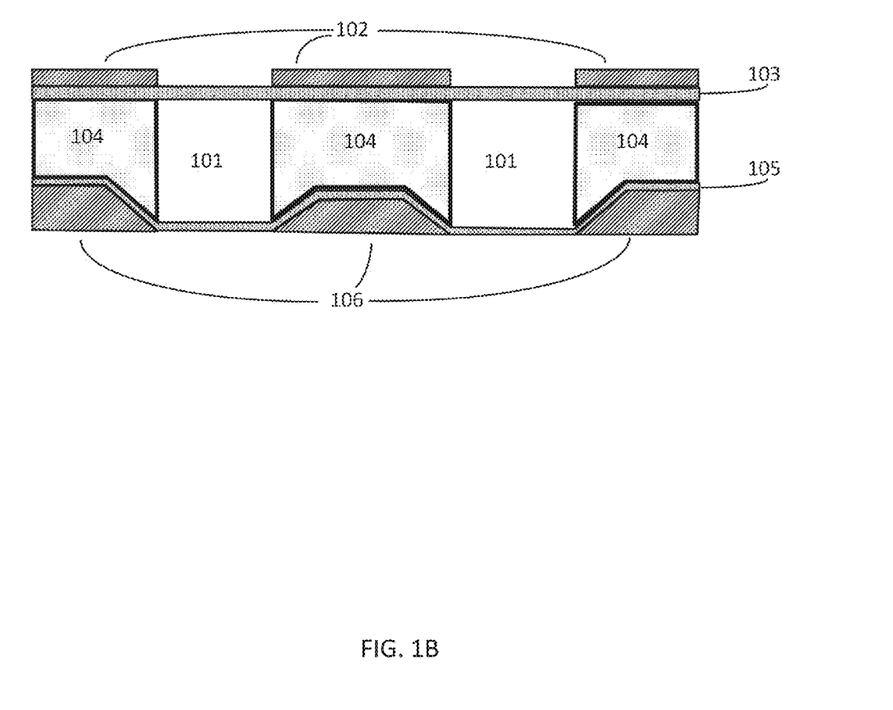
FIG. 1B shows a schematic cross-section of the cell pack, not to scale, illustrating the chamfers involved in making the membrane flush with the retaining plate.

FIG. 1B is a cross-sectional view through the wells 101 of an exemplary cell pack. The plastic main body 104 has inverse chamfers matched by chamfers in the bottom plate 106, which clamps the bottom membrane 105 to the body 104. The top plate 102 holds the top membrane 103 to the body 104.

Other suitable configurations can be used other than those described above, including modifications to those skilled in the art. For example, the materials used may be varied. Optionally, the chamfered features may be repeated on the top side of the pack as well. Preferably, at least one exterior surface of the cell pack features portions of a flexible membrane containing the cell culture well that is flush the an exterior, rigid surface of the cell pack.

While the system was tested to work with primary culture murine cortex cells, it should accommodate nearly any type of primary cell or cell line. Culture conditions can be adjusted for different cell types. Although collagen is used in the examples, other materials or combinations thereof may be used as an extracellular matrix (ECM). A 3D culture in ECM may have a thickness ranging from a thin layer of a few cells thick to several centimeters.

Brain Surrogate

An exemplary brain surrogate was manufactured in two pieces. The brain surrogate was divided into a front and a back half for use in testing frontal insults. It is desirable that forces are applied along the central axis of the culture wells, making them directional. Thus, embodiments involving testing insults from other orientations, laterally for example, would involve splitting the brain surrogate in an appropriate orientation.

Figure 2:
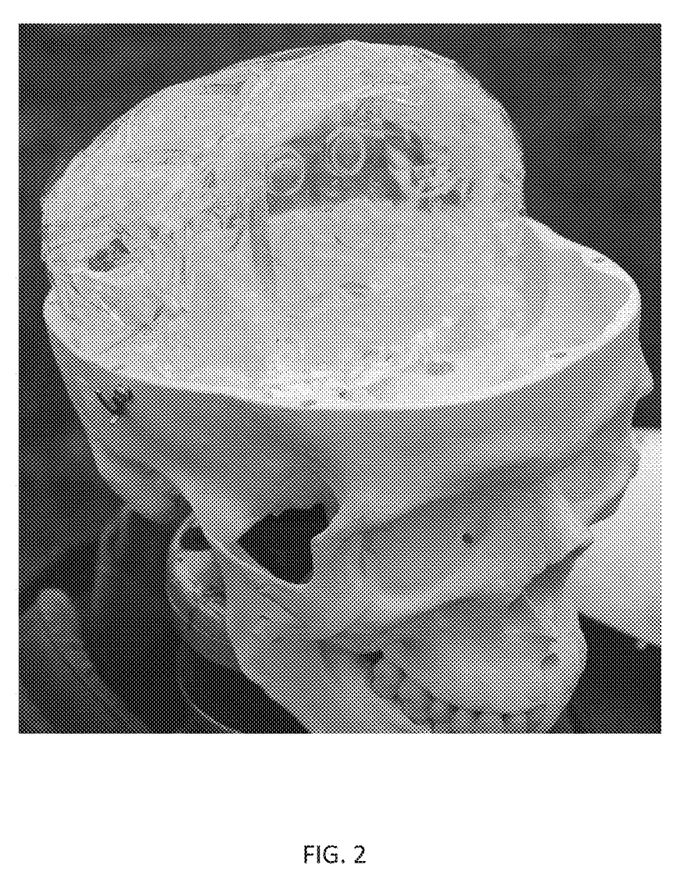
FIG. 2 shows a rear portion of a surrogate brain disposed inside a skull surrogate. This rear portion has a square-shaped pocket adapted to receive a cell pack including four posts to ensure good coupling into the cell culture wells—these posts fit into the recess of the top retaining plate and directly couple to the silicone gasket.

In order create the rear portion of the brain, a mold was made from the rear portion of one of a commercially available skulls used in the head surrogate. The mold was made such that the rear brain surrogate would completely fill the rear portion of the skull, keeping it in place when installed. A negative mold of the cell pack was attached to a crossbar and placed over the rear brain mold to form a pocket for the cell pack. The mold was then filled with Dow Corning Sylgard 184 mixed at a ratio of 1:37 (curing agent:elastomer) which was allowed to cure. This resulted in the rear brain surrogate piece being slightly stiffer than real brain tissue, but capable of holding the cell pack tightly and durable enough to survive multiple field tests (blasts or other tests) without special handling. This piece is shown in FIG. 2.

Figure 3:
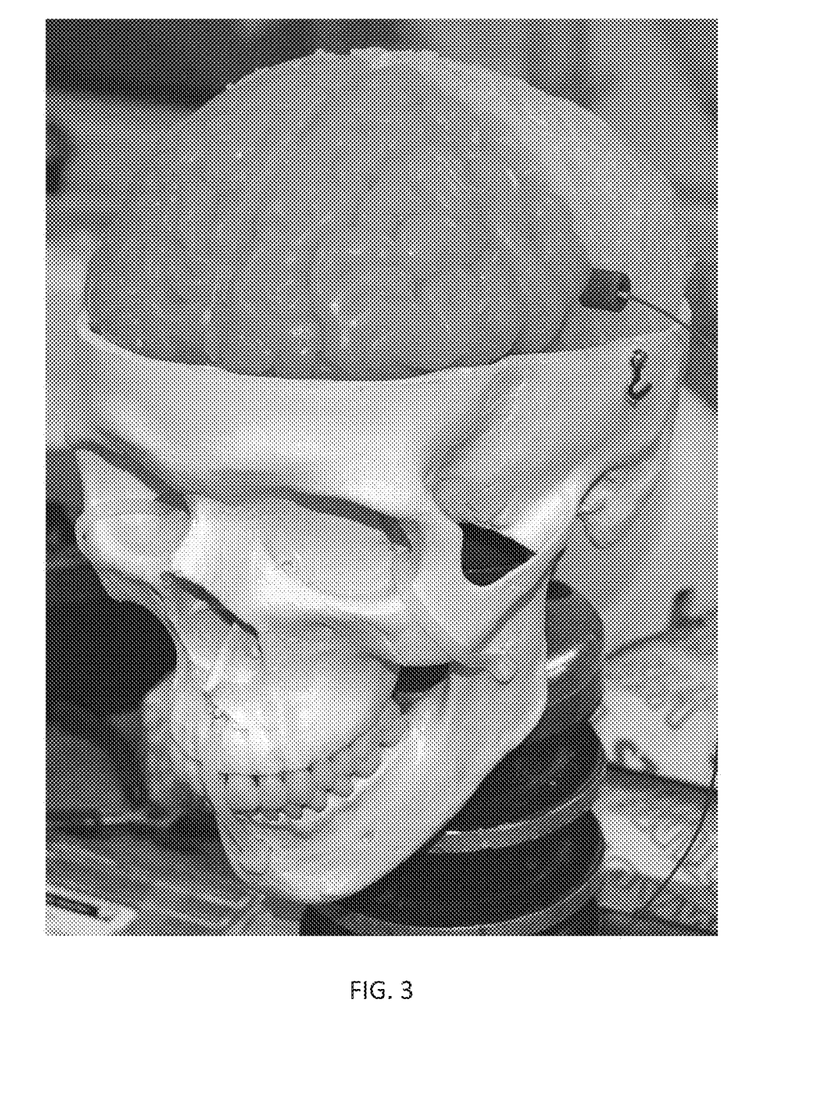
FIG. 3 shows a front portion brain surrogate in place in front of a rear portion brain surrogate together inside a skull surrogate. The material from which it is cast has a Young's modulus close to that of gray matter. The red cylinder and blue cable are part of a pressure sensor located in a test cell pack.

The front portion of the brain is made from a 50% by weight mixture of water and SIM-TEST (Corbins, White City, Oreg.). This results in a material with a Young's modulus close to that of gray matter in the brain and with a consistency close to that of brain tissue. The SIM-TEST mixture is cast in a mold made from a commercially available, anatomically correct plastic brain. The back face of this piece is flat and directly contacts the front of the culture chamber and the flush silicone rubber gasket to provide excellent acoustic coupling from the front brain surrogate piece through the cell culture to the back brain surrogate piece. The front brain surrogate is fragile, must be kept cool until use, and will grow mold if not kept clean. It is treated as a consumable item. However, it is an excellent mimic of live brain and since the front brain surrogate sits between the cell cultures and the insults, it is critical that this piece be as realistic as possible. The front brain surrogate is shown in FIG. 3.

Testing Configuration

The brain surrogate pieces were placed in a commercially available, anatomically accurate simulated skull made of plastic (3B Scientific Products, Tucker, Ga.) mounted on a standard DOT Hybrid III neck (Humanetics, Plymouth, Mich.). One or more sensors may be included inside or attached to the cell pack, for example sensors to measure pressure and/or acceleration. An example can be seen in FIG. 3. Once the cell pack was inserted, the skull cap (i.e., the top half of the skull model) was put in place and sealed with tape. A commercially available silicone skin can optionally be fitted over the skull/neck if desired. Given that this is a full sized surrogate system, any type of conventional or experimental head gear can be fitted for testing. Once the testing is complete, the skull cap and front brain piece were removed and the cell pack retrieved and returned to an incubator until the cell cultures are to be tested. Typically, cells were examined at 2 hrs, 1 day, and 4 days post insult.

The simulated skull preferably closely conforms to the shape and mass of a human skull, including a cranial cavity suitable to hold the brain surrogate. It may be made of plastic or another material such as a bone simulant.

The effect of the test on the cells may be analyzed using various techniques including electrophysiology, analysis of biochemical markers, and microscopic examination. In the practical examples, an MTT assay (Promega, Madison, Wis.) was used to determine overall cell culture metabolism. This assay has the benefit of being quick, simple, robust, and inexpensive. The basic assay can be performed in the field if needed, with the samples being taken back to the lab for final reading on a spectrophotometer.

Examples of tests that might be performed using such systems include drop tower (impact), ballistic tests (for example using projectiles), tests involving a shock tube, and/or free field blasts, including tests described in commonly-owned U.S. patent application Ser. No. 14/486,622 filed on Sep. 15, 2014 and incorporated herein by reference.

Figure 4A:
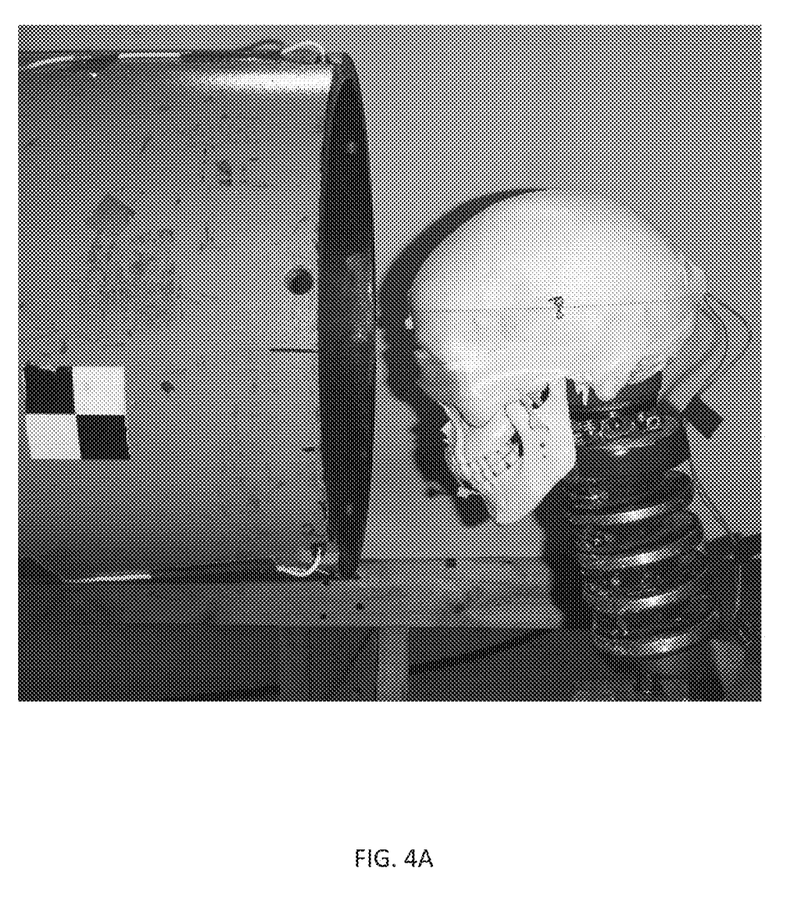
FIG. 4A shows an assembled head/brain surrogate positioned in front of a 12 inch shock tube. This image was from a pressure/acceleration test (the blue cables are from an accelerometer and pressure sensor located in an instrumented version of the cell pack.
Figure 4B:
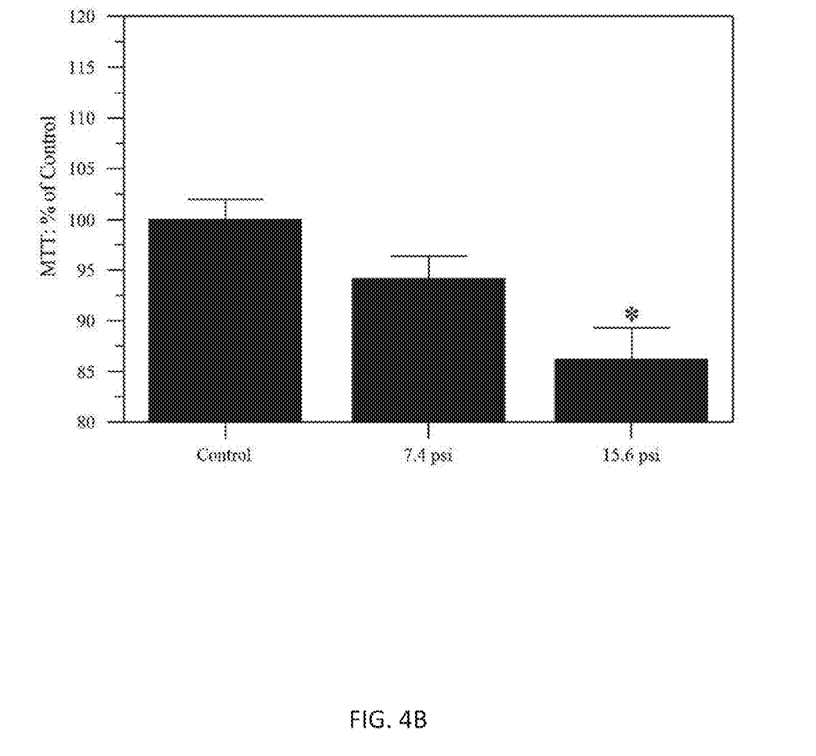
FIG. 4B shows results from a conventional 3-(4,5-dimethylthiazol-2-yl)-2,5-diphenyltetrazolium bromide (MTT) assay one day post insult. There was a statistically significant decrease in culture metabolism at the higher pressure.

The full head surrogate system was first tested using the 12 inch shock tube as shown in FIG. 4A. Cell packs contained within the head were exposed to levels of insult from the shock tube that resulted in peak overpressures measured within the cell packs reaching 7.4 and 15.5 psi, measured using a high resolution, high response optical pressure sensor (FISO Technologies, Québec, Canada). The results from experiments at these two pressures are shown in FIG. 4B. The lower overpressure resulted in a small (non-significant) reduction in cell culture metabolism at 1 day post-insult while the higher pressure resulted in a significant reduction of ~15% relative to control cultures.

The full head/brain surrogate system was also subjected to several free field blast tests. In this set of experiments, the head/brain surrogates were set up on stands that put the heads at ~5'8" off the ground. The explosive charge was hung at this height in the center of the arena and the surrogates were placed at two standoff distances from the explosive. Testing occurred both with and without helmets. Multiple blasts were carried out with a cycle time between blasts of less than 30 minutes. This included retrieving the just exposed cell packs and placing them in a portable incubator, removing the new cell packs from the portable incubator and placing in the surrogates, and prepping the surrogates for the next blast. Statistically significant differences were seen at 1 day post insult between the control cultures and the cultures at the two distances from the explosives. In addition, statistically significant differences were seen between bare heads and heads with helmets.

As a three-dimensional simulation of the human head with embedded live neurons, this system represents a new technique for testing the effects of blast, impact, and ballistic insults on living neurons and determining the effectiveness of protective head gear to mitigate this damage Animal models allow for the examination of living tissues, but fail to reproduce the geometry of the human head needed to properly evaluate protective head gear. In contrast, metal or gel-based models of the human head replicate the geometry, but provide no information about direct effects of the insult on the neural cells.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Arun P, Spadaro J, John J, Gharavi R B, Bentley T B, Nambiar M P. (2011) "Studies on blast traumatic brain injury using in-vitro model with shock tube." *Neuroreport* 22: 379-384.

Effgen G W, Hue C D, Vogel III E, Panzer M B, Meaney D F, Bass C R, Morrison III B. (2012) "A multiscale approach to blast neurotrauma modeling: part II: methodology for inducing blast injury to in vitro models." Frontiers in Neurology 3: 1-10.

What is claimed is:

1. A system for testing a helmet, the system comprising:
a simulated skull comprising a cranial cavity;
a brain surrogate disposed inside the cranial cavity; and
a cell pack comprising at least one culture well suitable for three-dimensional growth of live neurons therein, the cell pack comprising a rigid retaining plate having at least one opening exposing a portion of a flexible membrane containing the at least one cell culture well, the exposed membrane portion being substantially flush with an exterior surface of the retaining plate,
wherein the brain surrogate is configured to closely surround the cell pack inside the simulated skull.

2. The system of claim 1, further comprising a simulated skin on said simulated skull.

3. The system of claim 1, wherein said brain surrogate comprises two separable sections adapted to hold said cell pack therebetween.

4. The system of claim 3, wherein said separable sections are made of different materials.

5. The system of claim 1, further comprising a helmet.

6. The system of claim 1, further comprising a three-dimensional culture of live neurons within said at least one culture well.

7. The system of claim 6, further comprising at least one sensor inside or attached to said cell pack.

8. A method of testing a helmet, the method comprising:
providing a helmet testing system comprising
a simulated skull comprising a cranial cavity;
a brain surrogate disposed inside the cranial cavity; and
a cell pack comprising at least one culture well having a three-dimensional culture of live neurons therein, the cell pack comprising a rigid retaining plate having at least one opening exposing a portion of a flexible membrane containing the at least one cell culture well, the exposed membrane portion being substantially flush with an exterior surface of the retaining plate,
wherein the brain surrogate is configured to closely surround the cell pack inside the simulated skull; and
subjecting the helmet testing system to a physical insult; and
measuring a result of the physical insult.

9. The method of claim 8, further comprising placing said testing system in operational contact with a shock tube, and wherein said physical insult is a pressure wave.

10. The method of claim 8, further comprising placing said testing system in operational contact with a drop tower, and wherein said physical insult is an impact.

11. The method of claim 8, wherein said physical insult is a ballistic insult from a projectile.

12. The method of claim 8, wherein said physical insult is a free field blast.

13. The method of claim 8, wherein said measuring comprises conducting a metabolic assay on said neurons.

14. The method of claim 8, wherein said helmet testing system further comprises at least one sensor capable of measuring pressure and/or acceleration.

15. The method of claim 11, wherein said measuring comprises conducting a metabolic assay on said neurons.

* * * * *